United States Patent
Martinez

(10) Patent No.: US 6,812,404 B1
(45) Date of Patent: Nov. 2, 2004

(54) FEEDTHROUGH DEVICE HAVING ELECTROCHEMICAL CORROSION PROTECTION

(75) Inventor: Gonzalo Martinez, Mendota Heights, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 10/684,694

(22) Filed: Oct. 14, 2003

(51) Int. Cl.[7] .................................................. H01J 5/00
(52) U.S. Cl. ................................. 174/50.61; 174/50.64; 174/50.62; 174/50.52; 228/124.5
(58) Field of Search .................... 174/50.61, 50.64, 174/50.52, 152 GM, 52.3, 262, 50.62; 228/124.5; 429/181; 428/426

(56) References Cited

U.S. PATENT DOCUMENTS

| | | | | |
|---|---|---|---|---|
| 4,461,926 A | * | 7/1984 | Kyle ................... | 174/152 GM |
| 5,175,067 A | * | 12/1992 | Taylor et al. ............... | 429/181 |
| 5,272,283 A | * | 12/1993 | Kuzma ........................ | 174/262 |
| 5,368,220 A | * | 11/1994 | Mizuhara et al. ......... | 228/124.5 |
| 5,998,733 A | * | 12/1999 | Smith ....................... | 174/50.52 |
| 6,107,566 A | * | 8/2000 | Quadir et al. ............ | 174/50.52 |
| 6,674,001 B2 | * | 1/2004 | Marlor et al. ............ | 174/50.64 |

* cited by examiner

*Primary Examiner*—Dhiru R. Patel
(74) *Attorney, Agent, or Firm*—Girma Wolde-Michael; Paul H. McDowall

(57) ABSTRACT

Feed through assemblies and methods for their manufacture are provided. The feedthrough assemblies include a ferrule, an insulating material contacting the ferrule, and a terminal extending through the ferrule and having first and second areas separated by an area contacting the insulating material. A brazing material contacts the insulating material and the terminal's first area, and a conductive material covers the terminal's second area. The presence of the conductive material causes current density to be dispersed away from the brazing material.

20 Claims, 1 Drawing Sheet

FEEDTHROUGH DEVICE HAVING ELECTROCHEMICAL CORROSION PROTECTION

TECHNICAL FIELD

The present invention generally relates to feedthrough devices, and more particularly relates to extending the operating life of an apparatus that incorporates a feedthrough device by extending the operating life of the feedthrough device itself.

BACKGROUND

Electrical feedthrough assemblies provide a conductive path extending between the interior of a hermetically sealed container and a point outside the container. Electrical medical devices such as biorhythm sensors, pressure sensors, and implantable medical devices (IMD's) such as pulse generators and batteries often incorporate feedthrough assemblies. The conductive path comprises a conductive pin or other type of terminal that is electrically insulated from the container. Many feedthrough assemblies are known in the art, and typically include a ferrule, and an insulative material such as a glass or ceramic material, for positioning and insulating the pin within the ferrule. The reliability of the feedthrough assembly depends in large part on the durability of a hermetic seal between the various feedthrough assembly components. A hermetic seal is formed by heating and/or curing the insulating material, and may be strengthened by brazing the interfaces of the feedthrough assembly components using a brazing metal or alloy.

Feedthrough assemblies are subject to corrosion which can cause the seals to lose their hermeticity. When a feedthrough is functioning, the terminals are under continuous DC or AC bias. If the metal that brazes the glass/metal interface around the positive terminal is conductive, there is a likelihood that an anodic current density will be concentrated around the metal braze, causing the metal to corrode rapidly. In the case of a positive bias applied to the feedthrough pin, this is especially the case if the metal that forms the brazing is less passive (more conductive) than the pin. Moreover, there is a likelihood that the brazing around other glass/metal interfaces will be subject to corrosion as well. Corrosion of the metal brazing results in loss of hermeticity and the need for replacement of the feedthrough, or perhaps the entire device in which the feedthrough is incorporated.

In the case of batteries, organic electrolytes are a common cause of corrosion and cracking of both the insulating glass and the metal feedthrough components. Similar problems associated with corrosion are encountered with IMD's having feedthrough terminals that come into contact with body fluids.

Accordingly, it is desirable to improve the durability of feedthrough devices incorporating metal brazing to provide or strengthen a hermetic seal by lessening or eliminating corrosion of the metal brazing. It is also desirable to provide an improved feedthrough device and a method for making the same. In addition, it is desirable to provide an electrical device that incorporates an improved feedthrough device. Furthermore, other desirable features and characteristics of the present invention will become apparent from the subsequent detailed description and the appended claims, taken in conjunction with the accompanying drawings and the foregoing technical field and background.

BRIEF SUMMARY

A feedthrough assembly is provided for facilitating external electrical contact with an enclosed electrical circuit. The feedthrough assembly includes a ferrule, an insulating material contacting the ferrule, and a terminal extending through the ferrule and having first and second areas separated by an area contacting the insulating material. A brazing material contacts the insulating material and the terminal's first area, and a conductive material covers the terminal's second area. The presence of the corrosion resistant conductive material causes current density to be dispersed away from the brazing material.

A medical device is provided that incorporates a feedthrough assembly. The medical device includes an encasement, an electrical device disposed within the encasement, and the feedthrough assembly as described above. The feedthrough terminal is electrically coupled to the electrical device.

A method is provided for manufacturing a feedthrough assembly. The method includes the steps of covering a first area of a terminal with a conductive material, inserting the terminal through a ferrule, and surrounding an area of the terminal that is within the ferrule with an insulating material. A second area of the terminal and an adjacent region of the insulating material are then brazed with a brazing material. The brazing material is separated from the conductive material to thereby cause current density to be dispersed away from the brazing material.

A method is also provided for facilitating electrical contact with an electrical device disposed within a medical device having an encasement with an opening therein. The method comprises the steps of covering a first area of a terminal with a conductive material, inserting the terminal through a ferrule, and surrounding an area of the terminal that is within the ferrule with an insulating material. A second area of the terminal and an adjacent region of the insulating material are then brazed with a brazing material. The brazing material is separated from the conductive material to thereby cause current density to be dispersed away from the brazing material. The ferrule is then inserted into the encasement opening, and the terminal is electrically coupled to the electrical device.

BRIEF DESCRIPTION OF THE DRAWINGS

The present invention will hereinafter be described in conjunction with the following drawing figure, wherein like numerals denote like elements.

DETAILED DESCRIPTION

Figure 1:
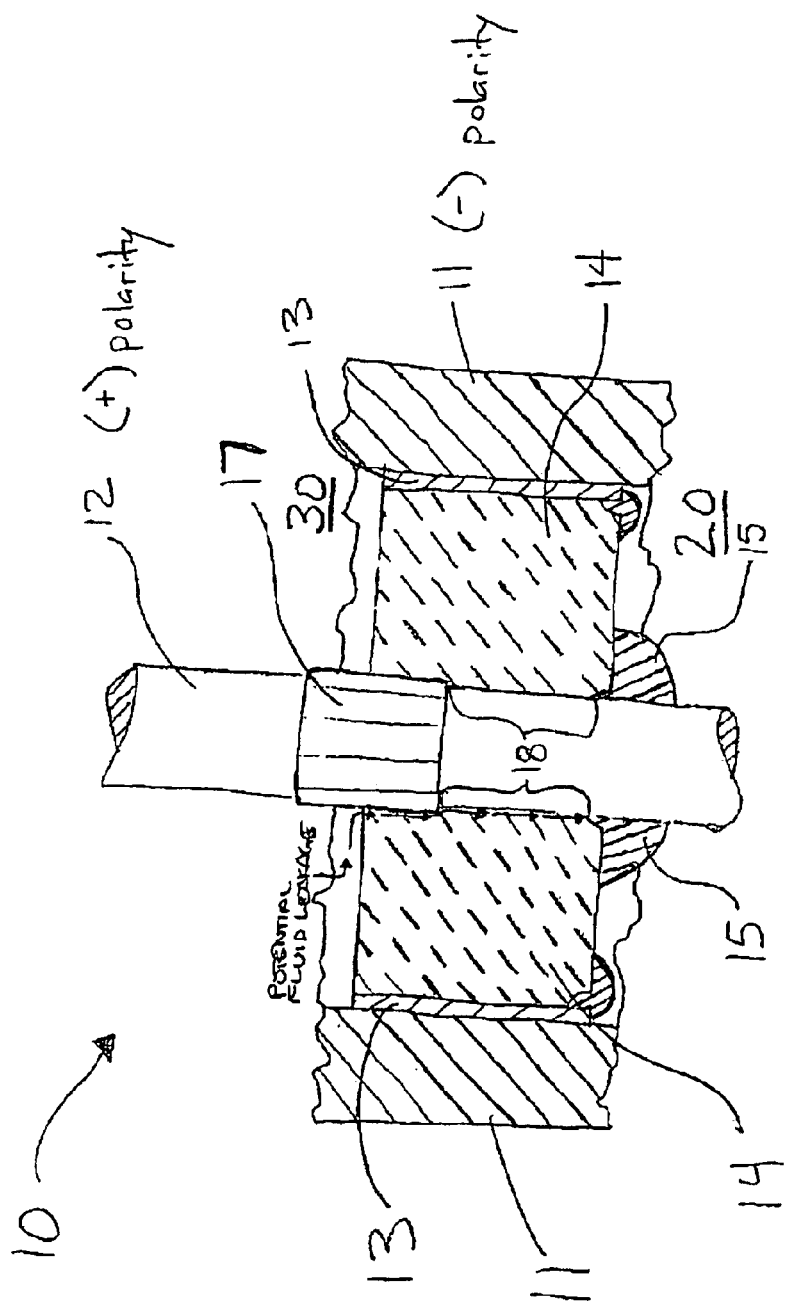
FIG. 1 shows a feedthrough device disposed installed in a medical device according to one embodiment of the present invention.

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

The various embodiments of the present invention include a feedthrough assembly with a corrosion-resistant terminal. Some applications for which a feedthrough assembly of the present invention has particular but not limited utility are in medical devices such as IMD's and various sensors such as biorhythm sensors and pressure sensors. The feedthrough 10 as shown in FIG. 1 is disposed in a position where a hermetic side 20 is located on one side of a hermetic seal, and a non-hermetic 30 side is located on the opposite side of the hermetic seal. The hermetic seal prevents passage of fluids through the feedthrough 10, and includes an insulator/metal seal along with a metal brazing around the glass/metal interfaces, which will be further explained below.

As shown in FIG. 1, the feedthrough of the present invention includes a center pin or terminal 12, with a portion of the length of the terminal 12 passing through an opening in a ferrule 13. Electrical feedthroughs that are used in sensors or body implanted devices may inadvertently come into contact with body fluids. Thus, it is desirable that the terminal 12 be made of a bio-stable material. For example, the terminal 12 may consist of or include niobium, titanium, tantalum, platinum, iridium, zirconium, nitrides of the metals, alloys of the metals, and other bio-stable metals. In a typical installation, one end of the terminal 12 extends into the interior or hermetic side 20 of the medical device container 11 and makes electrical contact with the contents thereof, and another end extends exteriorly of the IMD or sensor.

An insulating member or body 14 surrounds a portion of the terminal 12. In an exemplary embodiment of the invention, the insulating member is typically a glass such as sapphire, but can be made of any suitable ceramic-containing material or other electrically-insulative material such as diamond, ruby, zinc oxide, or even high dielectric polymers such as polyimides. The composition of the insulating member should be carefully selected to have thermal expansion characteristics that are compatible with the terminal 12. The insulating member 14 prevents a short circuit between the terminal 12 and the ferrule 13. Although in FIG. 1 the insulating member 14 is shown in contact with the terminal 12, there may be a micro-scale gap, on the order of approximately 1 μm between the two components.

In order to ensure a tight seal between the glass 14 and the walls of the container 11, the ferrule 13 is disposed as a thin sleeve therebetween. Typically the ferrule 13 has an annular configuration, but may have any configuration suitable for use with the container 11. The ferrule may be formed of titanium, niobium, platinum, molybdenum, tantalum, zirconium, vanadium, tungsten, iridium, rhodium, rhenium, osmium, ruthenium, palladium, any combination thereof, or any other suitable metal or combination of metals. The ferrule is affixed to the inner surface of the container 11 preferably by welding, although any other suitable means, such as gluing or soldering, may be used. A corrosion-resistant metal is preferably used to form the capsule or container 11, as the container will often be exposed to an oxidative environment.

As shown by the arrowed pathway in FIG. 1, fluids can potentially leak into the micro-scale gap between the glass 14 and the terminal 12. However, any such leakage is blocked from passage through the metal/glass seal due to a metal brazing 15 at the metal/glass interfaces. The metal that is used to braze about the glass/metal interfaces is typically gold, but can be any suitable corrosion resistant metal.

The terminal 12 is typically an anode terminal and is under continuous DC bias when in use. Consequently, when the terminal 12 is in a non-inert atmosphere, it is subject to surface oxidization over extended use. The terminal 12 is particularly subject to oxidation if it comes into contact with liquids such as water, blood, or other bodily fluids. As the inner surface of the terminal 12 becomes oxidized it becomes more insulative. Passivation of the terminal 12 can cause the metal braze 15 at the interface between the terminal 12 and the glass 14 to corrode, due to transfer of the current density from the passivated terminal 12 to the conductive metal that forms the metal braze 15. Corrosion of the metal braze 15 is worsened in the event that a fluid leaks into the micro-scale gap between the glass 14 and the terminal 12. Corrosion of the metal braze 15 can eventually cause the feedthrough device 10 to fracture and/or lose its hermeticity. For example, if the metal braze 15 is gold, potential corrosion of the metal braze can occur according to the formula:

In an exemplary embodiment of the present invention, the current density distribution around the metal braze 15 is significantly decreased by placing a conductive metal 17 having higher corrosion resistance than that of the metal braze 15 toward an opposite side of the glass 14 relative to the position of the metal braze 15. Placement of the conductive metal 17 on a surface of the terminal 12 that is opposite an interface 18 of the terminal and the glass relative to the position of the metal braze 15 reduces the current density on the metal braze 15.

Careful selection of a conductive metal 17 such that corrosion products of the conductive metal 17 are insoluble or of low solubility in aqueous chloride solutions provides additional assurance that the feedthrough device 10 will not fail due to dendritic growth or ionic pathway shorts between the terminal 12 and the ferrule 13. In an exemplary embodiment, the conductive metal is a platinum alloy, iridium, carbon, or other highly conductive metal.

The placement of the conductive metal 17 inside the protected feedthrough device 10 does not cause a dramatic increase in current leakage throughout the feedthrough device 10. The current is already somewhat inefficient due to the resistance created by the presence of solution about the feedthrough device 10, and particularly within the convoluted and thin pathway for leakage current shown by the arrowed pathway in FIG. 1. Consequently, the presence of the conductive metal results in a longer operating life for the feedthrough device 10, or any device that incorporates the feedthrough device 10, without impeding its performance during its operating life.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

What is claimed is:

1. A feedthrough assembly, which comprises:
   a ferrule;
   a terminal extending through said ferrule;
   an insulating body disposed within at least a portion of said ferrule and surrounding at least a portion of said terminal to insulate said terminal from said ferrule, said insulating body having a first end and a second end;
   a brazing material disposed proximate said first end and in contact with said terminal and said insulating body; and
   a conductive material disposed proximate said second end between said insulating body and said terminal to disperse current density from said brazing material.

2. A feedthrough assembly according to claim 1, wherein said insulating body contacts said conductive material.

3. A feedthrough assembly according to claim 1, wherein said conductive material is more conductive than said brazing material.

4. A feedthrough assembly according to claim 1, wherein said conductive material is, upon being subjected to corrosion, essentially insoluble in an aqueous chloride solution.

5. A feedthrough assembly according to claim 1, wherein said conductive material is selected from the group consisting of platinum, iridium, carbon, and alloys of platinum, iridium, or carbon.

6. A method of manufacturing a feedthrough assembly, which comprises the steps of:
   covering a first area of a terminal with a conductive material;
   surrounding a portion of said terminal with a ferrule;
   disposing an insulating material between said ferrule and said portion of said terminal that is surrounded by said ferrule; and
   applying a brazing material to a second area of said terminal and said insulating material with said brazing material, said brazing material being separated from said conductive material to thereby cause current density to be dispersed away from said brazing material.

7. A method according to claim 6, wherein said insulating material contacts said conductive material.

8. A method according to claim 6, wherein said conductive material is more conductive than said brazing material.

9. A method according to claim 6, wherein said conductive material is, upon being subjected to corrosion, essentially insoluble in an aqueous chloride solution.

10. A method according to claim 6, wherein said conductive material is selected from the group consisting of platinum, iridium, carbon, and alloys of platinum, iridium, or carbon.

11. A medical device, which comprises:
    an encasement;
    an electrical device disposed within said encasement; and
    a feedthrough assembly, comprising:
       a ferrule,
       a terminal extending through said ferrule and electrically coupled to said electrical device;
       an insulating body disposed within at least a portion of said ferrule and surrounding at least a portion of said terminal to insulate said terminal from said ferrule, said insulating body having a first end and a second end;
       a brazed material disposed proximate said first end and in contact with said terminal and said insulating body; and
       a conductive material disposed proximate said second end between said insulating body and said terminal to disperse current density from said brazing material.

12. A medical device according to claim 11, wherein said insulating material contacts said conductive material.

13. A medical device according to claim 11, wherein said conductive material is more conductive than said brazing material.

14. A medical device according to claim 11, wherein said conductive material is, upon being subjected to corrosion, essentially insoluble in an aqueous chloride solution.

15. A pressure sensor according to claim 11, wherein said conductive material is selected from the group consisting of platinum, iridium, carbon, and alloys of platinum, iridium, or carbon.

16. In a medical device having an encasement with an opening therein, and an electrical device disposed within said encasement; a method of facilitating external electrical contact with said electrical device, which comprises the steps of:
    covering a first area of a terminal with a conductive material;
    surrounding a portion of said terminal with a ferrule;
    disposing an insulating material between said ferrule and said portion of said terminal that is surrounded by said ferrule;
    applying a brazing material to a second area of said terminal and said insulating material with said brazing material, said brazing material being separated from said conductive material to thereby cause current density to be dispersed away from said brazing material;
    inserting said ferrule into said encasement opening; and
    coupling said terminal to said electrical device.

17. A method according to claim 16, wherein said insulating material contacts said conductive material.

18. A method according to claim 16, wherein said conductive material is more conductive than said brazing material.

19. A method according to claim 16, wherein said conductive material is, upon being subjected to corrosion, essentially insoluble in an aqueous chloride solution.

20. A method according to claim 16, wherein said conductive material is selected from the group consisting of platinum, iridium, carbon, and alloys of platinum, iridium, or carbon.

* * * * *

UNITED STATES PATENT AND TRADEMARK OFFICE
CERTIFICATE OF CORRECTION

PATENT NO. : 6,812,404 B1
DATED : November 2, 2004
INVENTOR(S) : Gonzalo Martinez It is certified that error appears in the above-identified patent and that said Letters Patent is hereby corrected as shown below:

Title page,
Item [57], ABSTRACT, delete "Feed through" and insert -- Feedthrough --.

Signed and Sealed this

Twenty-fourth Day of May, 2005

JON W. DUDAS
*Director of the United States Patent and Trademark Office*